United States Patent
Ushiyama et al.

(10) Patent No.: US 7,312,072 B2
(45) Date of Patent: Dec. 25, 2007

(54) MICROORGANISM CULTURE DEVICE AND MICROORGANISM CULTURE MEDIUM COMPRISING THE SAME

(75) Inventors: Masashi Ushiyama, Yokohama (JP); Shigeyuki Aoyama, Yokohama (JP)

(73) Assignee: Chisso Corporation, Osaka (JP)

(*) Notice: Subject to any disclaimer, the term of this patent is extended or adjusted under 35 U.S.C. 154(b) by 389 days.

(21) Appl. No.: 10/938,296

(22) Filed: Sep. 10, 2004

(65) Prior Publication Data

US 2005/0084948 A1  Apr. 21, 2005

Related U.S. Application Data

(63) Continuation of application No. 10/168,250, filed as application No. PCT/JP00/08923 on Dec. 15, 2000, now abandoned.

(51) Int. Cl.
*C12M 1/34* (2006.01)
*C12M 3/00* (2006.01)
*C12N 1/00* (2006.01)

(52) U.S. Cl. .................... 435/287.7; 435/243
(58) Field of Classification Search ............... None
See application file for complete search history.

(56) References Cited

U.S. PATENT DOCUMENTS 4,758,239 A   7/1988   Yeo et al.
5,439,010 A   8/1995   Ross

FOREIGN PATENT DOCUMENTS

EP      0 877 081       11/1998
JP      8 280377        10/1996
WO      WO 97/24432     7/1997

OTHER PUBLICATIONS

Sigma Catalog, 1997, pp. 284, 539-540, and 803.

*Primary Examiner*—Ralph Gitomer
*Assistant Examiner*—Bin Shen
(74) *Attorney, Agent, or Firm*—Merchant & Gould P.C.

(57) ABSTRACT

A microorganism culture device comprising a porous matrix layer having a basis weight of 40 to 100 g/m² and an air permeability of 7 to 24 cm/sec, and at least one layer of a water-soluble polymer layer laminated with the matrix layer.

17 Claims, 2 Drawing Sheets

Fig. 1

Plate count agar

MICROORGANISM CULTURE DEVICE AND MICROORGANISM CULTURE MEDIUM COMPRISING THE SAME

TECHNICAL FIELD

The present invention relates to a microorganism culture device for culturing and detecting microorganisms in foods and in environmental monitoring, and to a microorganism culture medium comprising the same. Further, the invention relates to a sheet-form microorganism culture device and a sheet-form microorganism culture medium comprising the same.

BACKGROUND ART

Microorganism culture tests, which have been performed in order to, for example, determine a total aerobic count in food test, have conventionally comprised the following steps: dissolving agar powder for preparing a culture medium; sterilizing the medium; storing the medium at approximately 45° C. to avoid solidification; injecting a certain volume of the medium into a sterilized petri dish containing a certain volume of a sample solution (for example, a suspension of a food); solidifying the agar after mixing; culturing at constant temperature; and counting the number of colonies of microorganisms. This conventional method of microorganism culturing involves not only preparing a culture medium in advance and sterilizing the medium, but also storing the medium at a sufficiently high temperature to avoid solidification, thereby requiring much time and labor.

Demand exists for omitting these time-consuming preparation steps in order to conduct simple and rapid microorganism culture test. In addition, glass and plastic petri dishes used for the tests involve problems. In food tests, which require numerous tests of microorganism culturing, cleaning and sterilizing glass petri dishes for reuse are very time consuming. Disposable sterilized plastic petri dishes have recently come into wide used, raising another problem of handling of a large volume of plastic wastes. For the determination of total aerobic counts in an environmental microorganism test, a conventional method includes the steps of wiping a certain area of a test subject with a piece of gauze or cotton bud; rinsing the gauze or cotton bud in sterilized water or saline to thereby obtain a suspension of the microorganisms adsorbed on the gauze or cotton bud; applying the suspension on a prepared agar medium or mixing and diluting the suspension with an agar medium as described above; culturing the microorganisms; and counting microorganism colonies. This method is also very time- and labor-intensive.

In order to solve those problems, simplified culture media which do not require preparation processes have been studied, manufactured, and commercially distributed. These simplified culture media may be classified into 4 types: a press type, a filter type, a film type, and a test paper type.

Japanese Patent Application Laid-Open No. 4-117299 discloses an test method using a press-type medium, which comprises the steps of dispensing an agar medium into a plastic container having a mound-like shape; and bringing the medium into direct contact with a test subject. The method is simple and useful for testing microorganism pollution in an environment; however, it cannot provide quantitative results, because the medium has a small surface area, and difficult to employed to test subjects having a curved or uneven surface, thereby making the method inapplicable to conventional food tests. Like the conventional method, the method also involves a problem of generating a lot of plastic waste after culturing, because plastic containers are used.

ANSI/ASTM F 488-79 describes a test method using a filter-type medium, which is typically a water-absorbent substance containing nutrients and covered with a membrane filter, the method comprising immersing the culture medium in a sample solution for impregnation; catching microorganisms on the filter surface; and culturing the microorganisms. The filter-type medium is suitable for liquid samples, but encounters difficulty in test of solid-containing samples.

In a known test method using a test-paper-type medium, a filter paper is impregnated with nutrients for promoting growth of microorganisms, and a sample solution is added to or absorbed by the filter paper, which is then stored in a plastic bag for culturing. However, the paper medium cannot provide quantitative results, because cultured colonies are likely to disperse and microorganisms grown inside the paper are difficult to observe.

Japanese Patent Publication No. 2-49705 and Application Laid-Open No. 3-015379 disclose test methods employing film-type media. These methods use a laminate of two films sandwiching a nutrient and a gelling agent, which is reconstituted to a gel when cold water is added thereto. Subsequently, microorganisms are incubated by dispensing a sample solution between the films. The film-type medium provides quantitative results in food tests and hence is useful. In environmental monitoring tests, however, bringing the medium into direct contact with a subject is difficult, unlike the press-type medium, and nutrients or gelling agents that are not firmly bonded are likely to scatter. Other disadvantages include leaking of a solution due to degradation and liquification of the gel that occur when microorganisms that degrade the gelling agent grow in the medium and liquefy the gel.

As described above, several types of simplified culture media for specific purposes have been developed and commercially distributed. However, none of them have been applicable to multiple purposes, including food tests and direct test of an environment.

Japanese Patent Application Laid-Open No. 6-181741 discloses a microorganism culture device comprising a laminate of a cold water-soluble gelling agent, and a water-absorbent fiber sheet. With the combination of a gelling agent and a water-absorbing fiber sheet in the microorganism culture device, a portion of an added sample solution is absorbed by the gelling agent, thereby preventing uniform distribution of the sample solution on the surface of the culture device. In addition, the culture device involves a problem in obtaining quantitative results, because microorganisms may fail to form colonies on a top surface of the water-absorbing fiber sheet, and microorganisms grown on the lower surface of the fiber sheet or inside the sheet are difficult to count. Therefore, for practical use, this type of microorganism culture device requires a water-absorbing fiber sheet that is sufficiently thin to be transparent or semitransparent, thereby enabling easy observation of the grown microorganisms. Another disadvantage is that this culture device is not suitable to test methods involving pressing or direct wiping, because the water-absorbing fiber sheet and the layer of the cold water-soluble gelling agent are not bonded.

The present inventors have disclosed in International Patent WO 97/24432 a sheet- or film-form microorganism culture medium comprising a porous matrix layer and a water-soluble polymer layer. The culture medium is useful for various purposes, including normal food tests and tests by wiping, produces small wastes, and can provide quantitative results. In this type of medium, a sample solution added into the porous matrix layer is temporarily retained in the porous matrix layer. The water-soluble polymer layer coming in contact with the porous matrix layer dissolves in water in the retained sample solution, and simultaneously nutrients for microorganism growth contained in the water-soluble polymer layer also dissolve in the water, thereby initiating microorganism growth. When the sample solution is added to the medium, the microorganisms in the solution disperse in the porous matrix layer but not inside the water-soluble polymer layer. This is because a high-viscosity layer formed by gradual dissolution of the water-soluble polymer layer surface prevents movement of the microorganisms into the water-soluble polymer layer. The dissolved water-soluble polymer layer and the porous matrix layer are homogenized, thereby pressing the microorganisms up to the porous matrix layer surface, where colonies are formed. Therefore, counting of microorganisms is relatively easy despite use of the porous matrix layer, because colonies are formed on the porous matrix layer surface.

However, despite the excellent features of the sheet- or film-form culture container or medium comprising a porous matrix layer and a water-soluble polymer layer, some drawbacks are involved, due to lack of optimal physical properties of the porous matrix layer specifically for culturing microorganisms. For example, some sample solutions exhibit poor dispensability of microorganisms or a smaller number of observable microorganisms growing in the medium as compared with the case of a standard method. In addition, in the case where a significant number of microorganisms are present, growth of the microorganisms may be impossible to observe. Therefore, prior to culturing microorganisms, a user of this sheet- or film-form culture container or medium must consider various factors, including retention of the sample solution, its dispensability, or permeability of the matrix layer to the water-soluble polymer that is dissolved by the sample solution. Further, in microbial tests involving numerous samples, time-consuming bag-packing of the medium is required after sample addition, in order to prevent unwanted microorganisms from contaminating the medium, and the packed media are bulky.

DISCLOSURE OF THE INVENTION

An object of the present invention is to provide a microorganism culture device which is suitable to conventional microbial tests for foods and an environmental monitoring and is easily applicable to microbial tests carried out on a curved or uneven surface as well as those carried out on a flat surface, by directly pressing or wiping test subjects, and to a microorganism culture medium comprising the same. A further object of the present invention is to provide a sheet-form microorganism culture device which is compact, easy to use, and capable of preventing contamination by unwanted microorganisms, as well as a sheet-form microorganism culture medium comprising the same.

The present inventors have conducted thorough research in an effort to solve the above-described problems and, as a result, have found that the objects are achieved by the means described below, thus leading to accomplishment of the present invention. Namely, the present invention provides the following.

(1) A microorganism culture device comprising a porous matrix layer having a basis weight of 40 to 100 g/m² and an air permeability of 7 to 24 cm/sec, and at least one layer of a water-soluble polymer layer laminated with the matrix layer.

(2) A microorganism culture device according to (1), characterized in that the water-soluble polymer layer comprises at least two sub-layers.

(3) A microorganism culture device according to (1) or (2) characterized in that when letters are assigned to the sub-layers of the water-soluble polymer layer in alphabetical order from the sub-layer nearest the porous matrix layer, the water-soluble layer comprises two sub-layers, Layer A and Layer B, wherein Layer A contains a water-soluble polymer and Layer B contains or consists of a water-soluble polymer.

(4) A microorganism culture device according to (1) or (2) characterized in that when letters are assigned to the sub-layers of the water-soluble polymer layer in alphabetical order from the sub-layer nearest the porous matrix layer, the water-soluble layer comprises three sub-layers, Layer A, Layer B, and Layer C, wherein Layer A and Layer B each contain a water-soluble polymer and Layer C consists of a water-soluble polymer.

(5) A microorganism culture device according to any of (1) to (4) characterized in that the water-soluble polymer in the water-soluble polymer layer contacting the porous matrix layer has a basis weight of 1 to 20 g/m².

(6) A microorganism culture device according to any of (1) to (5) characterized in that the water-soluble polymer is polyvinyl alcohol having a saponification degree of 75 to 95% and a molecular weight of 25,000 to 250,000.

(7) A microorganism culture device according to any of (1) to (6) characterized in that the porous matrix layer is a nonwoven fabric comprising at least one type of hydrophilic fiber selected from nylon, rayon, cotton, and cellulose.

(8) A microorganism culture device according to (7), characterized in that the porous matrix layer is a melt-blown nonwoven fabric of nylon.

(9) A microorganism culture device according to any of (1) to (8) characterized in that the porous matrix layer has a surface coating layer of a water-soluble material.

(10) A sheet-form microorganism culture device, characterized in that the microorganism culture device according to any of (1) to (9) is bonded at the center of an adhesive sheet larger than the microorganism culture device, with the porous matrix layer being an upper layer and a transparent film larger than the microorganism culture device covering the microorganism culture device by contacting the porous matrix layer and aligning the center of the transparent film on the microorganism culture device, wherein a transparent film area that does not contact the microorganism culture device, and an adhesive sheet area that is not bonded with the microorganism culture device are bonded together.

(11) A sheet-form microorganism culture device according to (10), characterized in that the adhesive sheet exhibits adhesion to the transparent film more strongly in some areas than in the remaining areas.

(12) A sheet-form microorganism culture device according to (10), characterized in that the adhesive sheet is partially bonded to the transparent film with pressure-sensitive adhesive tapes, which exhibit adhesion stronger than that of the pressure-sensitive sheet.

(13) A sheet-form microorganism culture device according to any of (10) to (12), characterized in that the adhesive sheet comprises a material selected from a polyester film having a thickness of 0.07 to 0.5 mm, a white polyester film, polyolefin-based synthetic paper, and polyolefin-laminated paper, and has on one side a coating layer of an acrylic pressure-sensitive adhesive or a rubber pressure-sensitive adhesive.

(14) A sheet-form microorganism culture device according to any of (10) to (13), characterized in that the transparent film is a polyolefin film or an easily peelable polyolefin film.

(15) A sheet-form microorganism culture device according to any of (10) to (14), characterized in that a thickness of the transparent film is 20 to 100 μm.

(16) A microorganism culture medium, characterized in that the microorganism culture device according to any of (1) to (9) contains at least one type of material selected from a nutrient for microorganism growth, a coloring agent, and a selective agent.

(17) A microorganism culture medium, characterized in that at least one type of material selected from a nutrient for microorganism growth, a coloring agent, and a selective agent is contained in Layer A and/or Layer B of the microorganism culture device according to (3) to (4).

(18) A microorganism culture medium, characterized in that a nutrient for microorganism growth, a salt, or a mixture thereof is contained in the water-soluble material according to (9).

(19) A microorganism culture medium, characterized in that at least one type of nutrient for microorganism growth is contained in the water-soluble polymer layer and/or the porous matrix layer of the microorganism culture device according to any of (1) to (9).

(20) A sheet-form microorganism culture medium, characterized in that at least one type of material selected from a nutrient for microorganism growth, a coloring agent, and a selective agent is contained in the sheet-form microorganism culture device according to any of (10) to (15).

(21) A sheet-form microorganism culture medium, characterized in that at least one type of nutrient for microorganism growth is contained in the water-soluble polymer layer and/or the porous matrix layer of the sheet-form microorganism culture device according to any of (10) to (15).

Reference Numerals

1: sheet-form microorganism culture device, 2: porous matrix layer, 3: transparent film, 4: adhesive sheet, 5: water-soluble polymer layer

BEST MODE FOR CARRYING OUT THE INVENTION

The present invention is described in detail as follows.

The microorganism culture device of the present invention comprises a laminate of a porous matrix layer having a basis weight of 40 to 100 g/m² and an air permeability of 7 to 24 cm/sec, and at least one layer of a water-soluble polymer, wherein the porous matrix layer is laminated on the water-soluble layer. In addition, the microorganism culture device is rarely kept outside during storage or culture, but is normally sealed in a container so as to prevent unwanted microorganisms from contaminating the culture device. In the present invention, a sheet-form microorganism culture device is provided by bonding the microorganism culture device at the center of an adhesive sheet larger than the microorganism culture device with the porous matrix layer serving as an upper layer, covering the microorganism culture device with a transparent film larger than the microorganism culture device by contacting the transparent film and the porous matrix layer and aligning the center of the transparent film on the microorganism culture device, and bonding a transparent film area that does not contact the microorganism culture device and an adhesive sheet area that is not bonded with the microorganism culture device. Namely, sealing the microorganism culture device in a sheet-form container provides a lightweight, compact, and easily handled sheet-form microorganism culture device. In the present invention, a microorganism culture device containing nutrients for microorganism growth is defined as a microorganism culture medium. Similarly, a sheet-form microorganism culture device containing nutrients for microorganism growth is defined as a sheet-form microorganism culture medium. The microorganism culture device and the sheet-form microorganism culture device are used as culture media by adding at least one type of nutrient for microorganism growth to the culture devices. Methods of adding the nutrient to the culture devices include adding the nutrient to the water-soluble polymer layer contacting the porous matrix layer in advance in the course preparation of the water-soluble polymer layer. Another method is adding on the porous matrix layer of the microorganism culture device a sample solution containing a nutrient during the course of test. The sample solution (water or water containing the nutrient for microorganism growth) added on the porous matrix layer is temporarily retained in the porous matrix layer, and the water-soluble polymer layer contacting the porous matrix layer is dissolved in the retained water. The resulting aqueous solution of the water-soluble polymer, together with the nutrient, is considered to provide a good environment for microorganism growth and initiates fission reproduction of the microorganisms. When the sample solution is added on the porous matrix layer, the microorganisms in the sample solution uniformly disperse throughout the entire porous matrix layer with the sample solution. The water-soluble polymer slowly dissolves to form a high-viscosity solution, which combines the water-soluble polymer layer and the porous matrix layer into one body. Thus, the microorganisms do not penetrate to the inside of the water-soluble polymer layer, but rather are pushed up to the porous-matrix layer surface, around which the microorganisms form colonies. This mechanism also functions for the microorganism culture device packed in a sheet-form container. For the microorganism culture medium having the porous matrix layer of a basis weight of 40 to 100 g/m² and an air permeability of 7 to 24 cm/sec, microorganism growth is easy to observe even when the number of the microorganisms is considerably large, because the fission reproduction occurs on or near the surface if the porous matrix layer. Therefore, the colony count is accurate in the present invention, despite use of a porous matrix layer.

Figure 3:
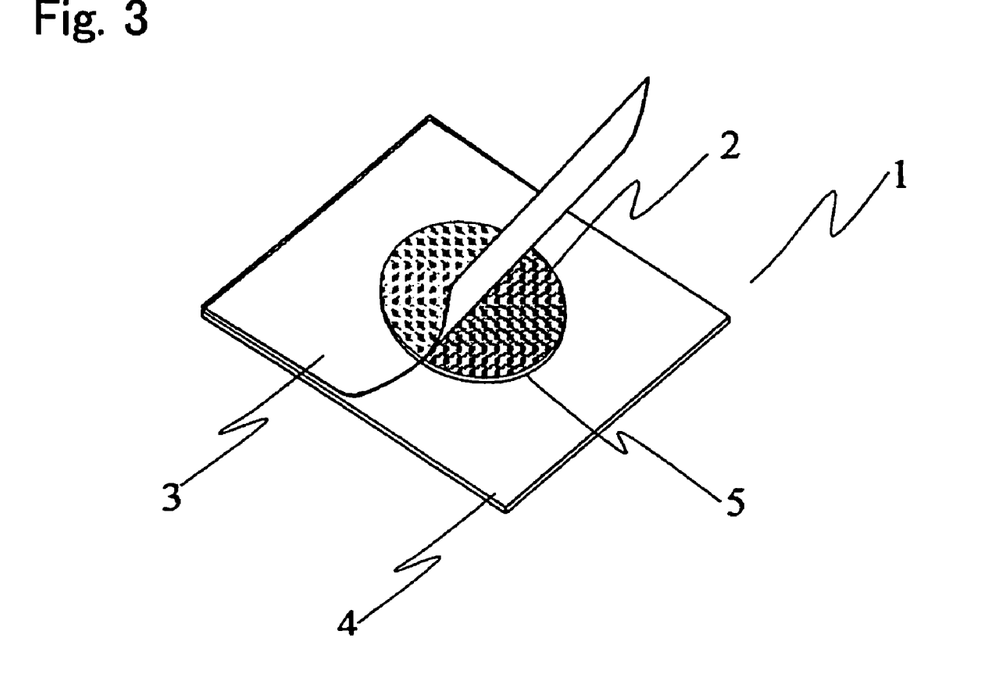
FIG. 3 is a schematic illustration of an example of the sheet-form microorganism culture device of the present invention.
Figure 4:
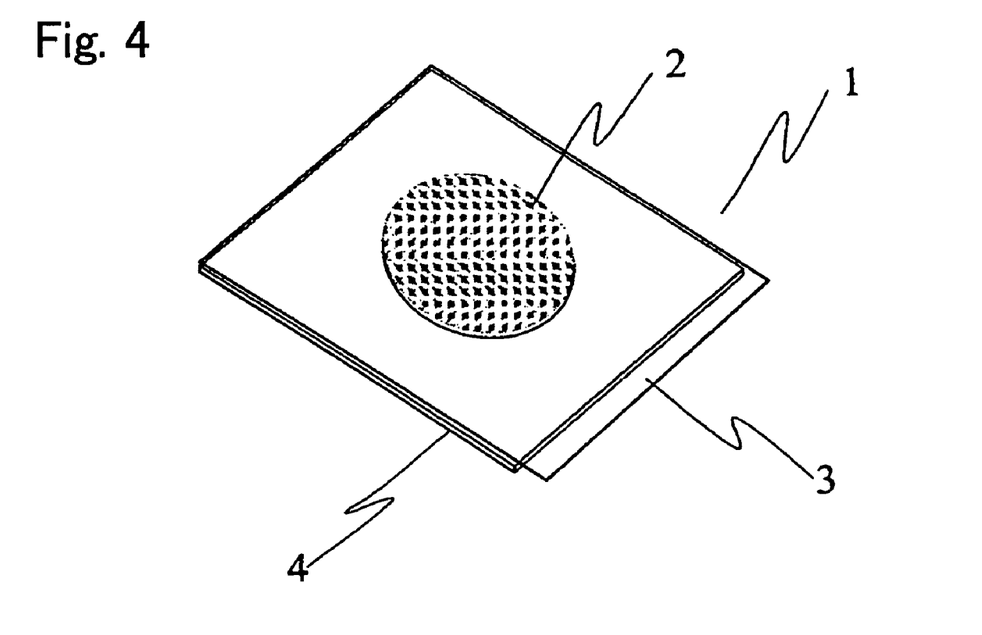
FIG. 4 is a schematic illustration of an example of the sheet-form microorganism culture device of the present invention.

The structures of the microorganism culture device and the sheet-form microorganism culture device of the present invention will now be described with reference to FIGS. 3 and 4. The sheet-form microorganism culture device (1) of the present invention comprises the microorganism culture device (5) bonded at the center of an adhesive sheet (4) larger than the microorganism culture device (5) with a porous matrix layer (2) serving an upper layer, and a transparent film (3) larger than the microorganism culture device (5) covering the microorganism culture device (5) by contacting the porous matrix layer (2) and aligning the center of the transparent film (3) on the microorganism culture device (5), wherein a transparent film area that does not contact the microorganism culture device (5) and an adhesive sheet area that is not bonded with the microorganism culture device (5) are bonded together.

Porous sheets or films are used for the porous matrix layer of the present invention. The basis weight of the porous matrix layer is preferably 50 to 90 g/m$^2$, more preferably 55 to 80 g/m$^2$. When the basis weight falls significantly below 40 g/m$^2$, the porous matrix layer cannot retain added water and sample solutions, possibly resulting in leakage of the sample solutions from the porous matrix layer or inhibition of formation of colonies in an easily observable form, owing to insufficient fixability of the high-viscosity solution of the dissolved water-soluble polymer layer. When the basis weight falls significantly above 100 g/m$^2$, the high-viscosity solution of the dissolved water-soluble polymer layer is retained inside the porous matrix layer, and hence the high-viscosity solution of the dissolved water-soluble polymer layer and the porous matrix layer are insufficiently bonded. This results in the possibility of microorganisms growing inside the porous matrix layer as well as on the surface of the porous matrix layer, possibly leading to difficulty in observing the microorganisms grown inside the porous matrix layer and slow growth of the microorganism near the porous matrix layer surface, due to lack of nutrition. Air permeability of the porous matrix layer is preferably 7 to 24 cm/sec [70 to 240 L/(m$^2$·sec)], more preferably 8 to 20 cm/sec, further preferably 10 to 18 cm/sec. When the air permeability falls significantly below 7 cm/sec, water components including a sample solution fail to be uniformly dispersed in the water-soluble polymer layer due to lack of water permeability of the porous matrix layer, possibly raising problems, including prevention of uniform culturing of the microorganisms. When the air permeability falls significantly above 24 cm/sec, the fixability of the high-viscosity solution of the dissolved water-soluble polymer layer becomes insufficient, which is likely to prevent the microorganisms from forming colonies in an easily observable form, causing an inaccurate microorganism count.

Fiber materials are used to prepare the porous matrix layer; for example, synthetic fibers including nylon fibers, polyacrylonitrile fibers, polyvinyl alcohol (PVA) fibers, ethylene-vinyl acetate copolymer fibers, polyester fibers (preferably hydrophilized), polyolefin fibers (preferably hydrophilized), and polyurethane fibers; semi-synthesized fibers such as rayon fibers; natural fibers including wool (animal fibers), silk, cotton fibers, cellulose fibers, and pulp fibers; and inorganic fibers such as glass fibers. Among these fibers, at least one type of fiber selected from nylon fibers, cotton fibers, cellulose fibers, and rayon fibers is preferably used for preparing the porous matrix layer. Porous sheets comprising woven fabrics or nonwoven fabrics of these fibers or porous films, sponges, porous ceramics, etc. made from the materials of the fibers listed above can also be used as the porous matrix layer. Porous sheets of woven fabrics or nonwoven fabrics whose basis weight and air permeability are easily adjusted are especially preferred. Further, melt-blown nylon nonwoven fabrics manufactured by a melt-blown method, by which fine fibers are manufactured with relative ease, or super-fine fiber nonwoven fabrics manufactured from separated fibers, are particularly preferred.

The porous matrix layer of the present invention may be water-repellent. However, a hydrophilic or hydrophilized porous matrix layer is preferred, because a water absorbing rate is higher than that for the water-repellent porous matrix layer, and hence the efficiency of the test work is enhanced. In addition, the surface of the porous matrix layer is preferably coated with a water-soluble material, because the dispensability of microorganisms is improved. For the water-soluble material, nutrients for microorganism growth and/or salts are preferably used, by virtue of their suitability to microorganism culture. Any water-soluble nutrient for microorganism growth that does not inhibit microorganism growth is used as the water-soluble material. Preferred examples of the water-soluble material include peptones, yeast extract, meat extract, casamino acids, amino acids, amino acid mixtures, saccharides including glucose or maltose, organic acids, and organic acid salts. Salts used for pH control or osmotic pressure control can also used as the water-soluble material without raising any problem. For example, hydrochloric acid salts such as sodium chloride, phosphoric acid salts such as dipotassium phosphate, and carbonic acid salts such as sodium bicarbonate are preferably used as the water-soluble material. The water-soluble material is coated on the porous matrix layer as a single component or a mixture. Although the nutrients or the salts can be sprayed as powders on the porous matrix layer, coating as a solution or a suspension is preferred. Any solvents that dissolve or partially dissolve the water-soluble materials can be used to prepare the solutions or the suspensions, and preferable examples are water, ethanol, methanol, and a mixture thereof.

As water-soluble polymers for preparing the water-soluble polymer layer of the present invention, polymers that dissolve in water to exhibit a viscosity of $1 \times 10^{-2}$ Pa·s or greater (at 40° C.) when a sample solution is added and that do not inhibit microorganism growth are preferably used. Examples include polyvinyl alcohol, cellulose derivatives, poly(acrylic acid) derivatives, starch derivatives, proteins, protein derivatives, and polysaccharides. Among these, polyvinyl alcohol is most preferable, especially polyvinyl alcohol having a saponification degree of 75 to 95% and a molecular weight of 25,000 to 250,000.

The microorganism culture device of the present invention contains at least one water-soluble polymer layer, wherein the water-soluble polymer layer is either a single layer or multiple layers. The multi-layered water-soluble polymer layer is prepared by coating the water-soluble polymer solutions a certain number of times. Alternatively, a certain number of water-soluble polymer sub-layers are prepared individually and are subsequently laminated to form the multi-layered water-soluble polymer layer. For example, the microorganism culture device preferably has a water-soluble polymer layer comprising Layer A and Layer B when letters are assigned to the water-soluble polymer sub-layers in alphabetical order from the one nearest the porous matrix layer, wherein Layer A contains a water-soluble polymer and Layer B contains or consists of a water-soluble polymer. In this case, Layer A preferably contains at least one type of material selected from a nutrient for microorganism growth, a coloring agent, and a selective agent, and Layer B either comprises only the water-soluble polymer or additionally contains at least one type of material selected from a nutrient for microorganism growth, a coloring agent, and a selective agent. In another example, the microorganism culture device preferably has a water-soluble polymer layer comprising Layer A, Layer B, and Layer C, wherein Layer A and Layer B each contain a water-soluble polymer and Layer C consists of a water-soluble polymer. In this case, at least one type of material selected from a nutrient for microorganism growth, a coloring agent, and a selective agent is preferably contained in Layer A and/or Layer B. In contrast, Layer C preferably comprises only the water-soluble polymer. Layer C, which is the water-soluble polymer sub-layer furthest from the porous matrix layer, comprising only the water-soluble polymer reduces the amount of a nutrient for microorganism growth to be added to the water-soluble polymer layer, resulting in sufficient use of the nutrient for microorganism growth. Incidentally, certain combinations of the coloring agents and the selective agents may cause a reaction when mixed. In order to prevent the reactions, Layer B is divided into multiple layers and reactive components are added separately to different layers. When the water-soluble polymer layer is multi-layered, the sub-layers are preferably bonded together tightly. Preparing a multi-layered water-soluble polymer layer comprising more than 5 sub-layers is not sensible, because doing so yields no positive effect corresponding to the accompanying increased cost and increased number of preparation steps.

In order to use the microorganism culture device of the present invention as a microorganism culture medium, a nutrient for microorganism growth is added to the water-soluble polymer layer in advance when the microorganism medium is prepared, or water containing the nutrient for microorganism growth is added when microorganisms are incubated, thus turning the microorganism culture device into a culture medium. In this case, for the microorganism culture device, favorable culture conditions are established by adding 350 to 650 mL of water containing the nutrient for microorganism growth per square meter of surface area of the microorganism culture device. Similarly, for the microorganism culture medium, favorable culture conditions are established by adding 350 to 650 mL of water or water containing the nutrient for microorganism growth per square meter of surface area of the microorganism culture medium. No particular limitations are imposed on nutrients for microorganism growth used in the present invention, so long as the nutrients are suitable for microorganisms. Examples include a standard liquid culture medium and a culture medium component prepared by removing agar from an agar culture medium. In addition, a selective agent for inhibiting growth of non-subject microorganisms, an indicator or a die for making colonies clearly visible, or a chromogenic or fluorogenic enzyme substrate for detecting a microorganism to be determined may be added.

The selective agents of the present invention include antibiotics, synthetic antibacterial agents, pigments, surfactants, and inorganic salts. Examples of the antibiotics include methicillin, cefmetazole, cefixime, ceftadizime, cefsulodin, bacitracin, polymyxin B, rifampicin, novobiocin, colistin, lincomycin, chloramphenicol, tetracycline, and streptomycin. Examples of the synthetic antibacterial agents include sulfonamides, nalidixic acid, and olaquindox. Examples of the pigments include crystal violet, brilliant green, malachite green, and methylene blue, all of which are bacteriostatic or bactericidal. Examples of the surfactants include Tergitol 7, dodecylsulfates, and laurylsulfates. Examples of the inorganic salts include selenites, tellurites, sulfites, sodium nitride, lithium chloride, oxalates, and concentrated sodium chloride. Further examples of the selective agents include taurocholates, glycin, bile extract, bile salts, and deoxycholates.

Examples of the nutrients for microorganism growth include, for enumeration of total aerobic counts, a mixture of yeast extract, peptone, and glucose; a mixture of meat extract and peptone; a mixture of peptone, soybean peptone, and glucose; and any of these mixtures further containing dipotassium phosphate and/or sodium chloride. Examples for enumeration of coliforms and/or *Escherichia coli* include a mixture of sodium desoxycholate, peptone, ferric ammonium citrate, sodium chloride, dipotassium phosphate, lactose, and neutral red; and a mixture of peptone, lactose, desoxycholate, peptone, eosin Y, and methylene blue. Examples for test of *Staphylococcus aureus* include a mixture of meat extract, peptone, sodium chloride, manit, phenol red, and yolk; and a mixture of peptone, meat extract, yeast extract, sodium pyruvate, glycin, lithium chloride, tellurites, and yolk. Examples for test of vibrio include a mixture of yeast extract, peptone, sucrose, sodium thiosulfate, sodium citrate, sodium cholate, ferric citrate, sodium chloride, ox bile, bromthymol blue, and thymol blue. Examples for test of *enterococci* include a mixture of ox brain extract, heart extract, peptone, glucose, dipotassium phosphate, sodium nitride, bromthymol blue, and 2,3,5-triphenyltetrazolium chloride. Examples for test of fungus include a mixture of peptone and glucose; a mixture of yeast extract and glucose; and a mixture of potato extract and glucose.

In order to make colonies clearly visible, tetrazolium salts such as 2,3,5-triphenyltetrazolium chloride or pH indicators are added to the water-soluble polymer layer so that a color develops or changes as microorganisms grow to thereby visibly indicate the microorganism growth. Further, adding coloring or fluorescent enzyme substrates for an enzyme contained in a specified microorganism enables detection of the microorganism. However, care should be taken in preparing the microorganism culture device or the microorganism culture medium, because these coloring agents are easily denatured by heat. In addition, tellurites or other components of Vogel-Johnson culture medium or Baird-Parker culture medium for *Staphylococcus aureus* should be added only after other components are sterilized and cooled in preparing the microorganism culture medium, due to their tendency of thermal degradation. Antibiotics are also generally prone to thermal degradation and should be added after cooling. When a water-soluble polymer solution is turned into a film- or sheet-form water-soluble polymer layer, a significant amount of water should be evaporated, and drying by heat or hot air takes a few minutes. Therefore, for example, in the case where the water-soluble polymer solution contains a tetrazolium salt, negative effects are caused by the drying process, including coloring of the tetrazolium salt, lowering effects of the tetrazolium salt by its thermal degradation, or inhibition of microorganism growth by a degraded tetrazolium salt. The water-soluble polymer solution is dried at a temperature sufficiently low and for a sufficiently short time such that negative effects of thermal denaturing or thermal degradation are not revealed if the concentration of the water-soluble polymer solution is 2 to 20% and the basis weight of the water-soluble polymer of the water-soluble polymer layer (content of the water-soluble polymer) is 1 to 20 g/m$^2$, although feasibility of this method depends on the components. Thus, the microorganism culture device or the microorganism culture medium containing components that are prone to thermal denaturing or thermal degradation is prepared by preparing in advance a water-soluble polymer layer containing components that are not prone to thermal denaturing or thermal degradation; coating on the layer a water-soluble polymer aqueous solution containing the components that are prone to thermal denaturing or thermal degradation; laminating the porous matrix layer on the coating; and drying. In the case of the single-layered water-soluble polymer layer, the basis weight of the water-soluble polymer of the water-soluble polymer layer (content of the water-soluble polymer) that contacts the porous matrix layer is preferably 1 to 20 g/m$^2$, more preferably 3 to 12 g/m$^2$, and in the case of the multi-layered water-soluble polymer layer, the basis weight is preferably 1 to 20 g/m$^2$, more preferably 1 to 10 g/m$^2$. When nutrients for microorganism growth are added to the water-soluble polymer layer in order to prepare the microorganism culture medium, the water-soluble polymer of the water-soluble polymer layer turns into a high-viscosity solution by dissolving in an added water solution, resulting in a slow diffusion rate of the nutrients for microorganism growth and possibly insufficient supply to microorganisms of the nutrients for microorganism growth. Thus, the nutrients for microorganism growth are likely to be consumed in insufficient quantity. In order to solve this problem, there is preferably used the multi-layered water-soluble polymer layer which contains a water-soluble polymer sub-layer, furthest from the porous matrix layer, having no nutrients for microorganism growth, and a water-soluble polymer sub-layer, contacting the porous matrix layer, having the nutrients for microorganism growth, because the nutrients for microorganism growth are concentrated around the growing microorganisms and high consumption efficiency of the nutrients is achieved. The water-soluble polymer sub-layer having no nutrients for microorganism growth preferably accounts for 20% or more of the entire water-soluble polymer layer, more preferably 40% or more. Although no upper limit is imposed on this value in terms of function, an upper limit of 80% is imposed when cost and workability are taken into account.

The microorganism culture device or the microorganism culture medium of the present invention may further contain a resin film laminated under the water-soluble polymer layer of the microorganism culture device or the microorganism culture medium. This resin film is a support film used in preparing the water-soluble polymer layer and may be removed from the water-soluble polymer layer as required. The material of the resin film is at least one type of resin selected from polyesters, polyolefins, and nylons. Use of the resin film comprising these resins is preferred, because adhesion to an adhesive sheet is improved. The microorganism culture device or the microorganism culture medium may be cut into any shape prior to use.

Any pressure-sensitive adhesive that does not interfere with microorganism growth is used for the adhesive sheets of the present invention. Among such adhesives, a pressure-sensitive adhesive with sufficiently weak adhesion for re-bonding the pressure-sensitive sheet and the transparent film is preferred, in view of good workability. Examples of such pressure-sensitive adhesives include rubber pressure-sensitive adhesives and acrylic pressure-sensitive adhesives, and peelable-type and low-adhesion-type acrylic pressure-sensitive adhesives are particularly preferable. General purpose thermoplastic resin sheets are used for a base sheet of the adhesive sheet, which needs to be rigid to some extent in order to afford easily peeling of the bonded transparent film yet sufficiently flexible for affording wiping on a curved surface. Examples include polyester films having a thickness of 0.07 to 0.5 mm, white polyester films, polyolefin-based synthetic paper, and polyolefin-laminated paper. The adhesive sheet may be in any shape, but must have an area that is not bonded with the microorganism culture device or the microorganism culture medium around the microorganism culture device, so that the adhesive sheet and the transparent film are tightly bonded at the bonding area with no gap therebetween.

Although any transparent film that does not interfere with microorganism growth is used for the transparent film of the present invention, flexible films are preferred, because the microorganism culture device or the microorganism culture medium is inserted between the adhesive sheet and the transparent film. Examples thereof include polyolefin films, polyester films, nylon films, and polyvinyl (chloride) films. Further, easily peelable films, which are treated with peeling agents, are also preferred, in view of enhancing peelability of the films. Among these, polyester films are preferred, and polyolefin films or easily peelable films are particularly preferred, in terms of workability such as opening and closing of the transparent films. The thickness of the transparent film is preferably 20 to 100 μm, in view of flexibility. The transparent film may be in any shape but must be larger than the microorganism culture device or the microorganism culture medium, so that the adhesive sheet and the transparent film are tightly bonded with no gap therebetween, so as to prevent penetration of unwanted microorganisms.

When the transparent film is peeled to open the sheet-form microorganism culture device or the sheet-form microorganism culture medium, the transparent film may be completely released from the adhesive sheet, but preferably the transparent film and the adhesive sheet are partially bonded together, because the transparent film must again cover the microorganism culture device or the microorganism culture medium and bond with the adhesive sheet. However, the transparent film may be removed when complete release of the transparent film from the sheet-form microorganism culture device or the sheet-form microorganism culture medium enhances workability in pressing or wiping tests. The adhesion strength between the transparent film and the adhesive sheet on the area where the microorganism culture device is not bonded is preferably stronger than in the remaining area, but sufficiently weak to be peeled, so that the transparent film is easily peeled to open for addition of sample solutions with a portion of the film bonded with the adhesive sheet and is bonded to reclose. Further, when the transparent film and the adhesive sheet are not completely bonded but have only an area with stronger adhesion than in the remaining area, the transparent film may be removed as required. The transparent film is preferably larger than the adhesive sheet, in view of easy opening of the transparent film.

Methods for making an area with strong adhesion in the adhesive sheet of the present invention include bonding the transparent film and the adhesive sheet with a pressure-sensitive adhesive tape having adhesion stronger than that between the adhesive sheet and the transparent film; bonding the transparent film and the adhesive sheet in one end with a double-sided adhesive tape; coating pressure-sensitive adhesives having different adhesion strengths; coating on the transparent film a pressure-sensitive adhesive having adhesion stronger than that between the adhesive sheet and the transparent film; and coating on an area where one end of the adhesive sheet and one end of the transparent film overlap a pressure-sensitive adhesive having adhesion stronger than that between the adhesive sheet and the transparent film in the remaining area. When a pressure-sensitive adhesive tape is used, preferably the adhesive sheet and the transparent film are shifted and the pressure-sensitive adhesive tape is bonded on both a pressure-sensitive adhesive side of the adhesive sheet and an area of the transparent film which does not contact the microorganism culture device or the microorganism culture medium, or on both the backside of the adhesive sheet and an area of the transparent film which contacts the microorganism culture device or the microorganism culture medium. In another preferable arrangement, without shifting the adhesive sheet and the transparent film, the pressure-sensitive adhesive tape is folded and bonded on both the backside of the adhesive sheet and an area of the transparent film which does not contact the laminated layers. When a the pressure-sensitive adhesive tape is folded and bonded on both the backside of the adhesive sheet and an area of the transparent film which does not contact the microorganism culture device or the microorganism culture medium, for the sake of convenience the transparent film may be completely removed from the adhesive sheet while the backside of the adhesive sheet and the transparent film remain bonded. The adhesion of the area with stronger adhesion should be stronger than that of the other area, preferably more than twice as strong.

Example preparation methods of the microorganism culture device and the sheet-form microorganism culture device of the present invention are described below.

An aqueous solution of a water-soluble polymer (the solution may optionally contain nutrients for microorganism growth and may optionally contain coloring agents or selective agents) is coated on a support film such as a polyester film, to provide a fully dried or partially-dried water-soluble polymer layer. Additional aqueous solutions of water-soluble polymers (the solutions may optionally contain nutrients for microorganism growth and may optionally contain coloring agents or selective agents) may be further coated on the water-soluble polymer layer as required, to form a multi-layered structure. Subsequently, a porous matrix layer is laminated on the water-soluble polymer layer and dried. When the water-soluble polymer layer has a multi-layered structure, the top sub-layer, contacting the porous matrix layer, of the water-soluble polymer layer preferably has a basis weight of 1 to 20 g/m$^2$. In the processes of laminating the porous matrix layer on the water-soluble polymer layer and drying, for the single-layered water-soluble polymer layer, the porous matrix layer is laminated on a partially-dried water-soluble polymer layer, or the porous matrix layer moistened with water or water containing the nutrients for microorganism growth is laminated on a fully dried water-soluble polymer layer. For the multi-layered water-soluble polymer layer, the water-soluble polymer solution is over-coated and the porous matrix layer is laminated immediately thereafter or after the water-soluble polymer solution is partially dried. Alternatively, the porous matrix layer is moistened with water or water containing the nutrients for microorganism growth and laminated on a fully dried water-soluble polymer layer. After the drying process, a water-soluble material may be coated on the porous matrix layer and dried, as required. The support film may be removed from the microorganism culture device as required. The microorganism culture device is then cut to a required size, bonded on a sheet or film coated with a pressure-sensitive adhesive, covered with a transparent film, placed in a bag or a petri dish, and sterilized with ethylene oxide gas, etc. to thereby prepare a sheet-form microorganism culture device. The microorganism culture medium is prepared by adding nutrients for microorganism growth to the microorganism culture device in the same manner as for the microorganism culture device. The sheet-form microorganism culture medium is also prepared in the same manner. The water-soluble polymer layer and the porous matrix layer are preferably bonded at least partially, regardless of the method employed to prepare the microorganism culture device or the microorganism culture medium.

A method for preparing the microorganism culture medium of the present invention having three-layered water-soluble polymer layer is exemplified below. The microorganism culture medium and the microorganism culture device are defined such that the microorganism culture medium contains nutrients for microorganism growth in Layer A and/or Layer B, whereas the microorganism culture device does not contain the nutrients for microorganism growth in these layers. A water-soluble polymer aqueous solution is coated on a resin film, such as a polyester film, and dried to form a water-soluble polymer sub-layer (Layer C). Another water-soluble polymer aqueous solution containing nutrients for microorganism growth, coloring agents, selective agents, or a mixture thereof is coated on the Layer C and dried to form a water-soluble polymer sub-layer (Layer B). Further, a water-soluble polymer aqueous solution containing nutrients for microorganism growth, coloring agents, or a mixture thereof is coated on Layer B to form a water-soluble polymer sub-layer (Layer A), thereby preparing a multi-layered water-soluble polymer layer comprising Layer C, Layer B, and Layer A. A porous matrix layer which may optionally contain culture medium components is laminated on the multi-layered water-soluble polymer layer and dried. The microorganism culture medium is prepared by the above-described processes. In this step, the basis weight of the water-soluble polymer in the water-soluble polymer sub-layer contacting the porous matrix layer is preferably 1 to 20 g/m$^2$. The porous matrix layer may be coated with an aqueous solution of nutrients for microorganism growth including peptone, yeast extract, meat extract, amino acid mixtures, and sugars or salts including sodium chloride, phosphates, and carbonates, or with an aqueous solution of a mixture of the nutrients and the salts, after which the aqueous solution is dried. The resin film used as a support film may be removed after the drying step, as required. The microorganism culture medium is then cut to an appropriate size and bonded on a larger adhesive sheet. In this step, the adhesive sheet is bonded on the resin film side of the microorganism culture medium when the resin film is not removed, and the adhesive sheet is bonded on the water-soluble polymer layer side when the resin film is removed. Subsequently, the microorganism culture medium is covered with a transparent film and the transparent film is bonded on the adhesive sheet in the area around the microorganism culture medium where the microorganism culture medium is not bonded. During or subsequent to this step, adhesion between the adhesive sheet and the transparent film at one end is made stronger than that between the adhesive sheet and the transparent film in the remaining area by shifting the transparent film and the adhesive sheet at one end and bonding a pressure-sensitive adhesive tape having adhesion stronger than that between the adhesive sheet and the transparent film; bonding the transparent film and the adhesive sheet in one end with a double-sided adhesive tape having adhesion stronger than that between the adhesive sheet and the transparent film; or coating on the transparent film, the adhesive sheet, or one end of the film and the sheet a pressure-sensitive adhesive having adhesion stronger than that of the remaining area. Finally, preparation of the sheet-form microorganism culture medium is completed by sterilizing with, for example, ethylene oxide gas.

The method for preparing the microorganism culture device or the microorganism culture medium of the present invention having a two-layered water-soluble polymer layer is exemplified as follows. The microorganism culture medium and the microorganism culture device are defined such that the microorganism culture medium contains nutrients for microorganism growth in Layer A and/or Layer B, whereas the microorganism culture device does not contain the nutrients for microorganism growth in these layers. A water-soluble polymer aqueous solution containing nutrients for microorganism growth, coloring agents, selective agents, or a mixture thereof, or an aqueous solution containing only the water-soluble polymer, is coated on a resin film, such as a polyester film, and dried to form a water-soluble polymer sub-layer (Layer B). Another water-soluble polymer aqueous solution containing, as required, nutrients likely to be denatured or decomposed by heat and coloring agents or their mixture, or an aqueous solution containing only the water-soluble polymer, is coated on Layer B to form a water-soluble polymer sub-layer (Layer A), to thereby prepare a multi-layered water-soluble polymer layer comprising Layer B and Layer A. A porous matrix layer which may contain nutrients for microorganism growth is laminated on the multi-layered water-soluble polymer layer and dried to thereby prepare the microorganism culture device or the microorganism culture medium. In this step, the basis weight of the water-soluble polymer in the water-soluble polymer sub-layer (Layer A) contacting the porous matrix layer is preferably 1 to 20 g/m$^2$. The resin film used as a support film may be removed after the drying step, as required. Subsequently, the microorganism culture device or the microorganism culture medium is cut to an appropriate size and bonded on a larger adhesive sheet. In this step, the adhesive sheet is bonded on the resin film side of the microorganism culture device or the microorganism culture medium when the resin film is not removed, and the adhesive sheet is bonded on the water-soluble polymer layer (Layer B) side when the resin film is removed. Subsequently, the microorganism culture device or the microorganism culture medium is covered with a transparent film, and the transparent film is bonded on the adhesive sheet in the area around or on the microorganism culture medium where the microorganism culture device or the microorganism culture medium is not bonded. During or subsequent to this step, adhesion between the adhesive sheet and the transparent film in one end is made stronger than that between the adhesive sheet and the transparent film in the remaining area, by shifting the transparent film and the adhesive sheet in one end and bonding a pressure-sensitive adhesive tape having adhesion stronger than that between the adhesive sheet and the transparent film; bonding the transparent film and the adhesive sheet in one end with a double-sided adhesive tape having adhesion stronger than that between the adhesive sheet and the transparent film; or coating on the transparent film, the adhesive sheet, or one end of the film and the sheet a pressure-sensitive adhesive having adhesion stronger than that of the remaining area. Finally, preparation of the sheet-form microorganism culture device or the sheet-form microorganism culture medium is completed by sterilizing with, for example, ethylene oxide gas.

Regardless of the method employed to prepare the sheet-form microorganism culture device or the sheet-form microorganism culture medium, the water-soluble polymer sub-layers themselves and the water-soluble polymer layer and the resin film when the resin film is not removed are preferably bonded, and the water-soluble polymer layer and the porous matrix layer are preferably at least partially bonded. Preferably, no gap is formed between the transparent film and the adhesive sheet in the bonded area.

The following are example methods of using the sheet-form microorganism culture medium are exemplified.

(1) For microbial test in foods, a sample food and a sterilized saline solution or sterilized water are homogenized in a sterilized bag with a stomacher, and the resulting suspension is diluted to an appropriate concentration to thereby prepare sample solutions. For environmental microbial monitoring; for example, a food manufacturing environment, a subject surface in a manufacturing site is wiped with a sterilized gauze or cotton bud, and the gauze, etc., is suspended in a sterilized saline solution or sterilized water. The resulting suspension is diluted to an appropriate concentration to thereby prepare a sample solution. The sheet-form microorganism culture device or the sheet-form microorganism culture medium is opened by peeling the transparent film (wherein the area with stronger adhesion is preferably left bonded), and the sample solution is added on the porous matrix layer. The microorganism culture medium is resealed by covering with the transparent film, and is incubated for a predetermined period at an appropriate temperature for culturing microorganisms. Subsequently, measurements including observation of microorganism growth and counting of microorganism colonies are carried out.

(2) A sterilized saline solution or sterilized water is added to the sheet-form microorganism culture medium of the present invention, and a subject surface is directly blotted or wiped with the sheet-form microorganism culture medium. A sterilized saline solution or sterilized water may be added again at this point. The sheet-form microorganism culture medium is covered with a transparent film (plastic films, etc.) so as to prevent evaporation of water, and microorganisms are incubated. Subsequently, measurements including observation of microorganism growth and counting of microorganism colonies are carried out.

(3) When a moist surface is tested, pre-moistening the sheet-form microorganism culture medium is not required. The surface is directly wiped or blotted with the sheet-form microorganism culture medium, which is then covered with a transparent film for culturing microorganisms. A sterilized saline solution or sterilized water may be added to the sheet-form microorganism culture medium prior to covering with the transparent film. Subsequently, measurements including observation of microorganism growth and counting of microorganism colonies are carried out.

(4) The sheet-form microorganism culture medium is left alone after a sterilized saline solution or sterilized water is added and falling microorganisms are caught on the sheet-form microorganism culture medium. Additional sterilized saline solution or sterilized water may be added at this point. The sheet-form microorganism culture medium is covered with a transparent film and the microorganisms are incubated. Subsequently, measurements including observation of microorganism growth and counting of microorganism colonies are carried out. As described above, the major feature of the sheet-form microorganism culture medium lies in its applicability to various microbial test methods, including direct contact with a test subject or wiping of a test subject, as well as to a conventional microbial test method for food or an environment. The test methods by direct contacting or direct wiping are applicable to a test subject having a curved surface or a surface having some extent of unevenness. For the sheet-form microorganism culture device, a sterilized saline solution or sterilized water containing nutrients for microorganism growth is used instead of a sterilized saline solution or sterilized water.

EXAMPLES

The present invention is further described in detail with reference to the following examples, which are not to be construed as restricting the scope of the present invention. The measurement methods employed in the following examples are described below.

(Microorganism Count)

Colonies formed on the microorganism culture medium are counted by eye observation.

(Air Permeability)

A porous matrix layer is tested according to a fragile method, a test method for nonwoven fabrics for medical use, provided in JIS L 1912 (unit: cm/sec).

(Basis Weight)

A porous matrix layer is cut into a square having sides measuring 20 cm and weighed. Subsequently, the weight is converted to weight per 1 m$^2$ (unit: g/m$^2$).

(Basis Weight of a Water-soluble Polymer in a Water-soluble Polymer Layer)

A water-soluble polymer layer is cut into a square having sides measuring 10 cm, dried, and weighed. Subsequently, the weight is converted to weight per 1 m$^2$ (unit: g/m$^2$). For the water-soluble polymer layer containing nutrients for microorganism growth, the weight of the nutrients is subtracted, on the basis of a proportional calculation. For the multi-layered water-soluble polymer layer, the weight is measured after each sub-layer is coated and dried, and the weight difference between the steps is calculated.

(Saponification Degree and Polymerization Degree of Polyvinyl Alcohol)

Saponification degree and polymerization degree of polyvinyl alcohol are determined according to the test method for polyvinyl alcohol provided in JIS K 6726-1994.

(Thickness)

Thickness of sheets and films is measured with Thickness Meter B1 (Toyo Seiki Seisaku-sho, Ltd.).

(Adhesion)

Adhesion is measured with a Tensilon-type tensile testing machine, according to a testing method for adhesive adhesion by de-lamination provided in JIS K 6854.

Example 1

Polyvinyl alcohol (degree of saponification: 89%, degree of polymerization: 1700, molecular weight: approximately 83,000) (45 g), meat extract (1.3 g), peptone (4 g), and dipotassium phosphate (1.3 g) were added to 0.75 L of water and heated for dissolution. The entirety of the solution was coated on a polyester film having a thickness 20 μm, a width of 0.5 m, and a length of 1 m (support resin film), and dried at 110° C. for 15 minutes to thereby prepare a polyvinyl alcohol film (Layer B of the water-soluble polymer layer). Subsequently, polyvinyl alcohol (degree of saponification: 89%, degree of polymerization: 1700, molecular weight: approximately 83,000) (5 g), meat extract (0.125 g), peptone (0.4 g), dipotassium phosphate (0.125 g), and 2,3,5-triphenyltetrazolium chloride (5 mg) were dissolved in 100 mL of water, and the entirety of the solution was coated on Layer B. A melt-blown nylon nonwoven fabric (porous matrix layer) having a basis weight of 65 g/m$^2$ and an air permeability of 12 cm/sec was laminated on the coating and dried at 100° C. for 30 seconds. The basis weight of the water-soluble polymer in the polyvinyl alcohol film contacting the melt-blown nylon nonwoven fabric (Layer A of the water-soluble polymer layer) was 9.8 g/m$^2$. The resulting laminate was then cut into a disk having a diameter of 50 mm, bonded on the polyester film (support film) side around the center of a pressure-sensitive adhesive polyester film having a thickness of 100 μm, a width of 70 mm, and a length of 80 mm; covered with a polypropylene film (transparent film) having a thickness of 0.06 mm, a width of 70 mm, and a length of 85 mm; and sterilized with ethylene oxide gas to thereby prepare the sheet-form microorganism culture medium, which was subsequently used as a culture medium for total aerobic counts.

Figure 1:
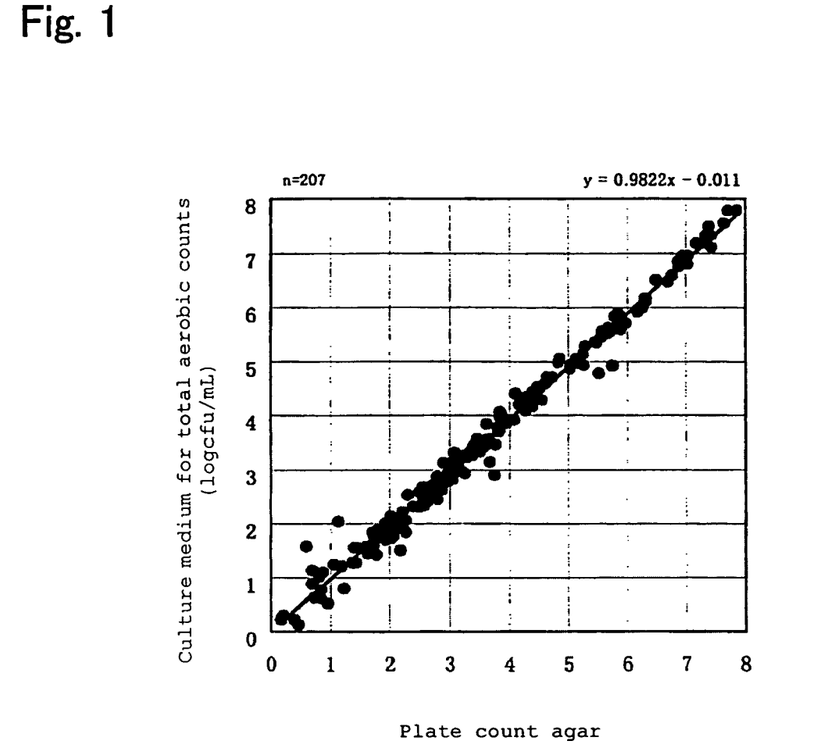
FIG. 1 is a graph comparing the performance of the culture medium for total aerobic counts used in Example 1 and that of a plate count agar.

Various foods (10 g) including meats, chopped vegetables, and cooked foods were placed in a sterilized bag, mixed with 100 mL of a sterilized saline solution, homogenized in a stomacher, and diluted ten-fold with a sterilized saline solution to thereby prepare a sample solution. The culture medium for total aerobic counts was opened by peeling the polypropylene film, and 1 mL of the sample solution was added. The culture medium was reclosed by covering with the polypropylene film, and microorganisms were incubated at 35° C. for 48 hours. Simultaneously, 1 mL of the sample solution was added in a sterilized petri dish and mixed with a plate count agar, which had been sterilized and stored at 45° C., and microorganisms were also incubated in the plate count agar at 35° C. for 48 hours. The microorganism counts for both of the media were compared. As shown in FIG. 1, the counts show good correlation, with a correlation coefficient of 0.999. The microorganism culture medium prepared by laminating a nonwoven fabric having a basis weight of 65 g/m$^2$ and an air permeability of 10 cm/sec comprising rayon, cotton, and cellulose instead of the melt-blown nylon nonwoven fabric was also used for similar microbial tests, and provided favorable microorganism culture.

*Escherichia coli* IFO 13500, *Bacillus subtilis* IFO 3134, *Staphylococcus aureus* IFO 13276, *Enterobacter cloacae* JCM 1232, *Providencia alcalifaciens* IFO 12931, and *Klebsiella oxytoca* JCM 1665 were incubated in a nutrient broth, and the medium was diluted with a sterilized saline solution to attain a concentration of 10$^4$ to 10$^8$/mL. The resulting sample solution (1 mL) was added to the prepared culture medium for total aerobic counts, and the microorganisms were incubated at 35° C. for 48 hours. For all the bacterial strains listed above, uniformly dispersed red spots were observed at a sample concentration of 10$^4$/mL, and the entire surface of the nonwoven fabric turned red at a sample concentration of 10$^5$/mL or higher.

Comparative Example 1

Polyvinyl alcohol (degree of saponification: 89%, degree of polymerization: 1700, molecular weight: approximately 83,000) (45 g), meat extract (1.3 g), peptone (4 g), and dipotassium phosphate (1.3 g) were added to 0.75 L of water and heated for dissolution. The entirety of the solution was coated on a polyester film having a thickness of 20 μm, a width of 0.5 m, and a length of 1 m (support resin film), and dried at 110° C. for 15 minutes to thereby prepare a polyvinyl alcohol film (water-soluble polymer layer). Subsequently, polyvinyl alcohol (degree of saponification: 89%, degree of polymerization: 1700, molecular weight: approximately 83,000) (5 g), meat extract (0.125 g), peptone (0.4 g), dipotassium phosphate (0.125 g), and 2,3,5-triphenyltetrazolium chloride (5 mg) were dissolved in 100 mL of water, and the entirety of the solution was coated on the film. A melt-blown nylon nonwoven fabric (porous matrix layer) having a basis weight of 105 g/m$^2$ and an air permeability of 6 cm/sec was laminated on the coating and dried at 100° C. for 30 seconds. The basis weight of the water-soluble polymer in the polyvinyl alcohol film (the water-soluble polymer layer) contacting the melt-blown nylon nonwoven fabric was 9.8 g/m$^2$. The resulting laminate was cut into a disk having a diameter 50 mm; bonded on the polyester film (support film) side around the center of a pressure-sensitive adhesive polyester film having a thickness 100 μm, a width of 70 mm, and a length of 80 mm; covered with a polypropylene film (transparent film) having a thickness of 0.06 mm, a width of 70 mm, and a length of 85 mm; and sterilized with ethylene oxide gas to thereby prepare the sheet-form microorganism culture medium, which was subsequently used as a culture medium for total aerobic counts.

Figure 2:
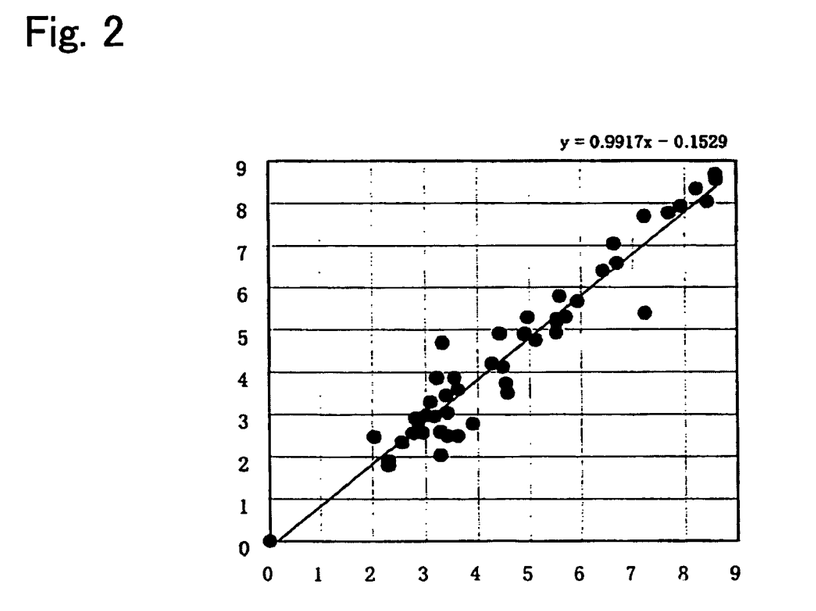
FIG. 2 is a graph comparing the performance of the culture medium for total aerobic counts used in Comparative Example 1 and that of a plate count agar.

As in Example 1, various foods (10 g) including meats, chopped vegetables, and cooked foods were placed in a sterilized bag, mixed with 100 mL of a sterilized saline solution, homogenized in a stomacher, and diluted tenfold with a sterilized saline solution to thereby prepare a sample solution. The culture medium for total aerobic counts was opened by peeling the polypropylene film, and 1 mL of the sample solution was added. The culture medium was reclosed by covering with the polypropylene film, and microorganisms were incubated at 35° C. for 48 hours. Simultaneously, 1 mL of the sample solution was added in a sterilized petri dish and mixed with a plate count agar, which had been sterilized and stored at 45° C., and microorganisms were also incubated in the plate count agar at 35° C. for 48 hours. The microorganism counts for both of the media were compared. As shown in FIG. 2, the counts showed fairly good correlation, with a correlation coefficient of 0.949; however, some samples of the sheet-form microorganism culture media showed aerobic count about one-tenth those obtained by the plate count agar.

*Escherichia coli* IFO 13500, *Bacillus subtilis* IFO 3134, *Staphylococcus aureus* IFO 13276, *Enterobacter cloacae* JCM 1232, *Providencia alcalifaciens* IFO 12931, and *Klebsiella oxytoca* JCM 1665 were incubated in a nutrient broth, and the medium was diluted with a sterilized saline solution to attain a concentration of 10$^4$ to 10$^8$/mL. The resulting sample solution (1 mL) was added to the culture medium for total aerobic counts, and the microorganisms were incubated at 35° C. for 48 hours. For *Escherichia coli*, *Enterobacter cloacae*, *Bacillus subtilis*, and *Klebsiella oxytoca*, color development was observed at a sample concentration of 10$^6$/mL or lower, but no color was observed at a sample concentration of 10$^7$/mL or higher. For *Staphylococcus aureus*, no color was observed at a sample concentration of 10$^6$/mL or higher, and for *Providencia alcalifaciens*, no color was observed at any sample concentration. The reasons for these results are considered to be slow supply of the nutrients for microorganism growth to the area where the microorganisms were growing, because the dissolved water-soluble polymer failed to reach the nonwoven fabric surface, thereby delaying microorganism growth. Another possible reason is that the nonwoven fabric interfered with observation of the colonies.

Example 2

Polyvinyl alcohol (degree of saponification: 89%, degree of polymerization: 1700, molecular weight: approximately 83,000) (30 g) was added to 0.5 L of water, and heated for dissolution. The entirety of the solution was coated on a polyester film having a thickness of 20 μm, a width of 0.5 m, and a length of 1 m (support resin film) and dried at 120° C. for 5 minutes to thereby prepare a polyvinyl alcohol film (Layer C of the water-soluble polymer layer). Subsequently, polyvinyl alcohol (degree of saponification: 89%, degree of polymerization: 1700, molecular weight: approximately 83,000) (15 g), peptone (3.75 g), dipotassium phosphate (1 g), lactose (0.2 g), and sodium deoxycholate (0.25 g) were dissolved in 250 mL of water, and the entirety of the solution was coated on Layer C and dried at 110° C. for 7 minutes to thereby prepare a polyvinyl alcohol film (Layer B of the water-soluble polymer layer) Further, polyvinyl alcohol (degree of saponification: 89%, degree of polymerization: 1700, molecular weight approximately 83,000) (4 g), peptone (1.25 g), dipotassium phosphate (0.25 g), lactose (0.05 g), and 5-bromo-4-chloro-3-indolyl-D-galactopyranoside (25 mg) were dissolved in 100 mL of water, and the entirety of the solution was coated on Layer B. A melt-blown nylon nonwoven fabric (porous matrix layer) having a basis weight of 65 g/m$^2$ and an air permeability of 10 cm/sec was laminated on the coating and dried at 100° C. for 30 seconds. The basis weight of the water-soluble polymer in the polyvinyl alcohol film contacting the melt-blown nylon nonwoven fabric (Layer A of the water-soluble polymer layer) was 7.8 g/m$^2$. The resulting laminate was cut into a disk having a diameter 50 mm; bonded on the polyester film (support film) side around the center of a pressure-sensitive adhesive polyester film having a thickness of 100 μm, a width of 70 mm, and a length of 80 mm; covered with a polypropylene film (transparent film) having a thickness of 0.06 mm, a width of 70 mm, and a length of 85 mm; and sterilized with ethylene oxide gas to thereby prepare the culture medium for coliforms.

*Escherichia coli* IFO 13500, *Klebsiella oxytoca* JCM 1665, *Klebsiella pneumoniae* JCM 1662, *Citrobacter freundii* IFO 12681, *Serratia rubidaea* IFO 12973, and the bacteria strain 1 and 2 isolated from foods were incubated in a nutrient broth, and the medium was diluted with a sterilized saline solution to attain a concentration of 10 to 500 cfu/mL. The diluted bacteria sample solution (1 mL) was added to the culture medium for coliforms, and the microorganisms were incubated at 36° C. Clearly visible blue spots were developed for all the bacterial strains after about 16 hours.

Comparative example 2

Polyvinyl alcohol (degree of saponification: 89%, degree of polymerization: 1700, molecular weight: approximately 83,000) (45 g), peptone (10 g), dipotassium phosphate (1.2 g), lactose (0.25 g), and sodium deoxycholate (0.3 g) were added to 0.75 L of water and heated for dissolution. The entirety of the solution was coated on a polyester film having a thickness of 20 μm, a width of 0.5 m, and a of length 1 m (support resin film), and dried at 110° C. for 20 minutes to thereby prepare a polyvinyl alcohol film (water-soluble polymer layer). Subsequently, polyvinyl alcohol (degree of saponification: 89%, degree of polymerization: 1700, molecular weight: approximately 83,000) (4 g), peptone (0.5 g), dipotassium phosphate (0.1 g), lactose (0.025 g), and 5-bromo-4-chloro-3-indolyl-D-galactopyranoside (25 mg) were dissolved in 100 mL of water, and the entirety of the solution was coated on the film. A melt-blown nylon nonwoven fabric having a basis weight of 65 g/m$^2$ and an air permeability of 10 cm/sec was laminated on the coating and dried at 100° C. for 30 seconds. The basis weight of the water-soluble polymer in the polyvinyl alcohol film (water-soluble polymer layer) contacting the melt-blown nylon nonwoven fabric was 7.8 g/m². The resulting laminate was then cut into a disk having a diameter 50 mm; bonded on the polyester film (support film) side at around the center of a pressure-sensitive adhesive polyester film having a thickness of 100 μm, a width of 70 mm, and a length of 80 mm; covered with a polypropylene film (transparent film) having a thickness of 0.06 mm, a width of 70 mm, and a length of 85 mm; and sterilized with ethylene oxide gas to thereby prepare a culture medium for coliforms.

*Escherichia coli* IFO 13500, *Klebsiella oxytoca* JCM 1665, *Klebsiella pneumoniae* JCM 1662, *Citrobacter freundii* IFO 12681, *Serratia rubidaea* IFO 12973, and bacterial strain 1 and 2 isolated from foods were incubated in a nutrient broth, and the medium was diluted with a sterilized saline solution to attain a concentration of 10 to 500 cfu/mL. The diluted bacteria sample solution (1 mL) was added to the culture medium for coliforms, and the microorganisms were incubated at 36° C. Development of clearly visible blue spots took about 16 hours for *E. coli* IFO 13500 and bacteria strain 1 isolated from foods; about 20 hours for *K. oxytoca* JCM 1665 and *S. rubidaea* IFO 12973; about 25 hours for *K. pneumoniae* JCM 1662 and *C. freundii* IFO 12681; and about 30 hours for bacterial strain 2 isolated from foods.

Example 3

Polyvinyl alcohol (degree of saponification: 89%, degree of polymerization: 1700, molecular weight: approximately 83,000) (30 g) was added to 0.5 L of water and heated for dissolution. The entirety of the solution was coated on a polyester film having a thickness of 20 μm, a width of 0.5 m, and a length of 1 m (support resin film), and dried at 120° C. for 5 minutes to thereby prepare a polyvinyl alcohol film (Layer C of the water-soluble polymer layer). Subsequently, polyvinyl alcohol (degree of saponification: 89%, degree of polymerization: 1700, molecular weight: approximately 83,000) (15 g), peptone (3.75 g), dipotassium phosphate (1 g), lactose (0.2 g), and sodium deoxycholate (0.25 g) were dissolved in 0.25 L of water, and the entirety of the solution was coated on Layer C and dried at 110° C. for 7 minutes to thereby prepare a polyvinyl alcohol film (Layer B of the water-soluble polymer layer). Further, polyvinyl alcohol (degree of saponification: 89%, degree of polymerization: 1700, molecular weight: approximately 83,000) (5 g), peptone (1.25 g), dipotassium phosphate (0.25 g), lactose (0.05 g), and 5-bromo-4-chloro-3-indolyl-D-galactopyranoside serving as a coloring agent (25 mg) were dissolved in 100 mL of water, and the entirety of the solution was coated on Layer B. A melt-blown nylon nonwoven fabric (porous matrix layer) having a basis weight of 65 g/m² and an air permeability of 12 cm/sec was laminated on the coating and dried at 100° C. for 30 seconds to thereby prepare the microorganism culture medium. The polyvinyl alcohol film contacting the melt-blown nylon nonwoven fabric serves as Layer A of the water-soluble polymer layer. The culture medium was then cut into a disk having a diameter 50 mm. A weak adhesion-type acrylic pressure-sensitive adhesive (manufactured by Lintec Corporation) was coated on a white polyester sheet having a thickness of 100 μm, a width of 80 mm, and a length of 90 mm to thereby prepare an adhesive sheet, and the disk-shaped microorganism culture medium was bonded on the polyester film at around the center. Subsequently, the adhesive sheet was covered by a polypropylene film (transparent film) having a thickness of 0.06 mm, a width of 80 mm, and a length of 90 mm, with the polypropylene film shifted by 5 mm in the longitudinal direction, and the shifted portion was covered by 90 mm-wide bag sealing tape (manufactured by Kyowa Limited Co., Ltd.). The resulting culture medium was sterilized with ethylene oxide gas to thereby prepare the sheet-form microorganism culture medium for the coliforms. The prepared sheet-form microorganism culture medium was very compact.

When the sheet-form microorganism culture medium was opened by peeling the polypropylene film (transparent film) from the side opposite the end that had been bonded with the bag sealing tape, peeling of the polypropylene film was stopped at the area of 5 mm width where the bag sealing tape had been bonded. Therefore, tasks such as sampling of microorganisms were carried out while the polypropylene film and the adhesive sheet were left bonded.

The sheet-form microorganism culture medium was opened by peeling the polypropylene film (transparent film) from the side opposite the end that had been bonded with the bag sealing tape, and 1 mL of a sample solution, which had been prepared by suspending food wastes in a sterilized saline solution and diluting as appropriate, was added to the culture medium. When the peeled polypropylene film was placed back on the adhesive sheet, the polypropylene film and the adhesive sheet were easily re-bonded.

The sheet-form microorganism culture medium was opened by peeling the polypropylene film (transparent film) from the side opposite the end that had been bonded with the bag sealing tape until peeling was stopped, and subsequently the polypropylene film was further peeled more strongly so to remove the polypropylene film from the adhesive sheet with the bag sealing tape still bonded on the polypropylene film. After 0.4 mL of a sterilized saline solution was added on the porous matrix layer, a chopping board was wiped with the sheet-form microorganism culture medium. Then, 0.6 mL of a sterilized saline solution was further added, and the peeled polypropylene film was placed back on the adhesive sheet. Although the bag sealing tape was not re-bonded, due to its deformation, the polypropylene film was re-bonded to the adhesive sheet with no gap therebetween. After the sheet-form microorganism culture medium was incubated at 36° C. for culturing, blue spots were observed due to the presence of the coliforms, indicating that the sheet-form microorganism culture medium is useful as a microorganism culture medium.

INDUSTRIAL APPLICABILITY

The microorganism culture device and the microorganism culture medium of the present invention comprise at least one layer of a water-soluble polymer and a porous matrix layer laminated on the water-soluble polymer layer, and the porous matrix layer has a basis weight of 40 to 100 g/m² and an air permeability of 7 to 24 cm/sec. By virtue of this structure, no preparation prior to microorganism culture is needed and hence, microbial tests for foods and environments are easily carried out. In addition to food tests or environmental tests that are carried out conventionally, subjects having a curved or uneven surface can also tested by pressing or wiping. Moreover, microorganisms in a sample solution disperse evenly on the surface of the microorganism culture medium, and therefore observation of the microorganisms is easy even when the number of the microorganisms is significantly large. Further, because the microorganism culture medium is thin, space required for storage and culturing is small, and waste is greatly reduced in volume as compared with the case of a conventional microorganism culture medium. In addition, because the water-soluble polymer layer is multi-layered and the basis weight of the water-soluble polymer in the water-soluble polymer sub-layer contacting the porous matrix layer is 1 to 20 g/m², components prone to thermal degradation can be added to the water-soluble polymer layer. Furthermore, because nutrients for microorganism growth are not added to the water-soluble polymer sub-layer that is furthest from the porous matrix layer when the water-soluble polymer layer comprises 2 or more sub-layers, the amount of added nutrients that are not taken up by microorganisms is reduced, uptake efficiency of the nutrients is increased, and the preparation processes are simplified.

With the sheet-form microorganism culture device and the sheet-form microorganism culture medium of the present invention, microbial tests for foods and environments are easily carried out, and test subjects with a curved or uneven surface can also be tested by direct pressing or wiping. Because the cover film may be partially bonded or completely removed during the course of a test, the most suitable method is selected in accordance with purposes, resulting in simple and easy microbial tests for various subjects and purposes. Further, because the sheet-form microorganism culture device and the sheet-form microorganism culture medium of the present invention assume the form of a thin sheet, space required for storage is small and waste is greatly reduced in volume as compared with the case of conventional microbial tests.

What is claimed is:

1. A microorganism culture device comprising a porous matrix layer having a basis weight of 40 to 100 g/m² and an air permeability of 7 to 24 cm/sec, and at least one water-soluble polymer layer laminated with the matrix layer.

2. A microorganism culture device according to claim 1, characterized in that the water-soluble polymer layer comprises at least two water-soluble polymer sub-layers.

3. A microorganism culture device according to claim 2, characterized in that when letters are assigned to the sub-layers of the water-soluble polymer layer in alphabetical order from the sub-layer nearest the porous matrix layer, the water-soluble layer comprises two sub-layers, Layer A and Layer B, wherein Layer A contains a water-soluble polymer and Layer B contains a water-soluble polymer.

4. A microorganism culture device according to claim 2, characterized in that when letters are assigned to the sub-layers of the water-soluble polymer layer in alphabetical order from the sub-layer nearest the porous matrix layer, the water-soluble layer comprises three sub-layers, Layer A, Layer B, and Layer C, wherein Layer A and Layer B contain a water-soluble polymer and Layer C consists of a water-soluble polymer.

5. A microorganism culture device according to claim 1, characterized in that the water-soluble polymer in the water-soluble polymer layer contacting the porous matrix layer has a basis weight of 1 to 20 g/m².

6. A microorganism culture device according to claim 1, characterized in that the water-soluble polymer is polyvinyl alcohol having a saponification degree of 75 to 95% and a molecular weight of 25,000 to 250,000.

7. A microorganism culture device according to claim 1, characterized in that the porous matrix layer is a nonwoven fabric comprising at least one type of hydrophilic fiber selected from nylon, rayon, cotton, and cellulose.

8. A microorganism culture device according to claim 7, characterized in that the porous matrix layer is a melt-blown nonwoven fabric of nylon.

9. A microorganism culture device according to claim 1, characterized in that the porous matrix layer has a surface coating layer of a water-soluble material.

10. A sheet-form microorganism culture device, characterized in that the microorganism culture device according to claim 1 is bonded at the center of an adhesive sheet larger than the microorganism culture device, with the water soluble polymer layer proximate the adhesive sheet and a transparent film larger than the microorganism culture device covering the microorganism culture device by contacting the porous matrix layer and aligning the center of the transparent film on the microorganism culture device, wherein a transparent film area that does not contact the microorganism culture device and an adhesive sheet area that is not bonded with the microorganism culture device are bonded together.

11. A sheet-form microorganism culture device according to claim 10, characterized in that the adhesive sheet adheres to the transparent film in some areas stronger than that in the remaining areas.

12. A sheet-form microorganism culture device according to claim 10, characterized in that the adhesive sheet is partially bonded to the transparent film with adhesive tapes, which adhere to the transparent film more strongly than to the sheet.

13. A sheet-form microorganism culture device according to claim 10, characterized in that the adhesive sheet comprises a material selected from a polyester film having a thickness of 0.07 to 0.5 mm, a white polyester film, polyolefin-based synthetic paper, and polyolefin-laminated paper and has on one side a coating layer of an acrylic adhesive or a rubber adhesive.

14. A sheet-form microorganism culture device according to claim 10, characterized in that the transparent film is a polyolefin film or an easily peelable polyolefin film.

15. A sheet-form microorganism culture device according to claim 10, characterized in that a thickness of the transparent film is 20 to 100 μm.

16. A microorganism culture device according to claim 2, characterized in that when letters are assigned to the sub-layers of the water-soluble polymer layer in alphabetical order from the sub-layer nearest the porous matrix layer, the water-soluble layer comprises two sub-layers, Layer A and Layer B, wherein Layer A contains a water-soluble polymer and Layer B contains a water-soluble polymer.

17. A microorganism culture device according to claim 2, characterized in that when letters are assigned to the sub-layers of the water-soluble polymer layer in alphabetical order from the sub-layer nearest the porous matrix layer, the water-soluble layer comprises three sub-layers, Layer A, Layer B, and Layer C, wherein Layer A and Layer B contain a water-soluble polymer and Layer C consists of a water-soluble polymer.

* * * * *